United States Patent
Schmotzer et al.

(10) Patent No.: US 9,265,507 B2
(45) Date of Patent: Feb. 23, 2016

(54) FEMORAL SLIDEWAY

(75) Inventors: Hans Schmotzer, Kolliken (CH); Peter Schuler, Karlsruhe (DE); Udo Malzer, Karlsruhe (DE)

(73) Assignee: Smith & Nephew Orthopaedics AG, Rotkreuz (CH)

(*) Notice: Subject to any disclaimer, the term of this patent is extended or adjusted under 35 U.S.C. 154(b) by 1147 days.

(21) Appl. No.: 11/953,819

(22) Filed: Dec. 10, 2007

(65) Prior Publication Data

US 2008/0091209 A1 Apr. 17, 2008

Related U.S. Application Data

(60) Continuation of application No. 10/616,102, filed on Jul. 9, 2003, now Pat. No. 7,306,609, which is a division of application No. 09/517,674, filed on Mar. 2, 2000, now abandoned.

(30) Foreign Application Priority Data

Mar. 2, 1999 (DE) .............................. 299 03 766 U
Apr. 16, 1999 (DE) .............................. 299 06 909 U

(51) Int. Cl.
*A61B 17/15* (2006.01)
*A61F 2/38* (2006.01)
(Continued)

(52) U.S. Cl.
CPC ........... *A61B 17/155* (2013.01); *A61F 2/30767* (2013.01); *A61F 2/3859* (2013.01); *A61F 2002/30013* (2013.01); *A61F 2002/30324* (2013.01); *A61F 2002/30616* (2013.01); *A61F 2002/30892* (2013.01); *A61F 2002/30929* (2013.01); *A61F 2002/4658* (2013.01);
(Continued)

(58) Field of Classification Search
CPC ............................. A61F 2/3859; A61B 17/155
USPC ........................................................ 623/20.35
See application file for complete search history.

(56) References Cited

U.S. PATENT DOCUMENTS

| 3,816,855 A | 6/1974 | Saleh |
| 4,944,756 A | 7/1990 | Kenna |

(Continued)

FOREIGN PATENT DOCUMENTS

| DE | 4041920 A1 | 6/1991 |
| DE | 19716879 A1 | 11/1998 |

(Continued)

OTHER PUBLICATIONS

Search Report for Counterpart German Application, Jan. 19, 2000, DE 299 06 909.5.

(Continued)

*Primary Examiner* — Bruce E Snow
*Assistant Examiner* — Melissa Hoban
(74) *Attorney, Agent, or Firm* — Taft Stettinius & Hollister LLP

(57) ABSTRACT

A femoral slideway and femoral slideway/femur-size template combination is employed to create an installed knee prosthesis that creates a reduced amount of stress in the collateral ligaments relative to previous prosthesis. In one embodiment, the reduced stress is achieved by employing a femoral slideway/femur-size template combination which results in installation of a femoral slideway which has a smaller dorsal-ventral dimension than a corresponding dimension of the femur prior to resection.

23 Claims, 4 Drawing Sheets

(51) Int. Cl.
*A61F 2/30* (2006.01)
*A61F 2/46* (2006.01)

(52) U.S. Cl.
CPC . *A61F 2250/0024* (2013.01); *A61F 2250/0036* (2013.01); *A61F 2310/00407* (2013.01)

(56) References Cited

U.S. PATENT DOCUMENTS

| | | |
|---|---|---|
| 5,116,338 A | 5/1992 | Poggie et al. |
| 5,326,361 A | 7/1994 | Hollister |
| 5,549,684 A | 8/1996 | Amino et al. |
| 5,549,688 A | 8/1996 | Ries et al. |
| 5,688,280 A | 11/1997 | Booth, Jr. et al. |
| 5,776,201 A | 7/1998 | Colleran et al. |
| 5,810,831 A | 9/1998 | D'Antonio |
| 6,123,729 A * | 9/2000 | Insall et al. ............... 623/20.31 |
| 6,152,960 A * | 11/2000 | Pappas ..................... 623/20.31 |
| 6,364,911 B1 | 4/2002 | Schmotzer et al. |
| 2004/0059426 A1 | 3/2004 | Schmotzer et al. |

FOREIGN PATENT DOCUMENTS

| | | |
|---|---|---|
| EP | 0 707 839 A1 | 4/1996 |
| EP | 0 765 645 A2 | 4/1997 |
| EP | 1 033 117 A3 | 1/2003 |
| WO | WO 94/26212 | 11/1994 |
| WO | WO 95/35074 | 12/1995 |
| WO | WO 97/30661 | 8/1997 |

OTHER PUBLICATIONS

German Search Report dated Nov. 14, 2002 for EP 1033117.

* cited by examiner

FEMORAL SLIDEWAY

CROSS-REFERENCE TO RELATED APPLICATIONS

This Application is a continuation application of U.S. application Ser. No. 10/616,102, filed on Jul. 9, 2003, which is a divisional application of U.S. patent application Ser. No. 09/517,674, filed on Mar. 2, 2000, now abandoned, the entire contents of which are incorporated herein by reference and should be considered a part of this specification. U.S. patent application Ser. No. 09/517,674 is based on and claims priority under 35 U.S.C. §119 to German Patent Applications DE 29906909.5, filed Apr. 16, 1999, and DE 29903766.5, filed on Mar. 2, 1999, the entire contents of which are incorporated by reference and should be considered a part of this specification.

BACKGROUND OF THE INVENTION

1. Field of the Invention

The invention relates to a femoral slideway, and more specifically to a femoral slideway/femur-size template arrangement and a knee endoprosthesis system with such a femoral slideway.

2. Description of the Related Art

A femoral slideway of this kind is disclosed, for example, in the German patent DE 40 41 002 C2. In the surgical technique customarily used for knee-joint replacement by means of such a femoral slideway, an equal amount of bone is removed from the two condyles of the femur, so that the anterior or ventral cut is parallel to the posterior or dorsal cut. When the implant is in the position thus defined, the axis of rotation of the implant no longer coincides with the axis specified by the arrangement of the collateral ligaments, and this position is not anatomical inasmuch as when flexed, the implant is seated either too tightly on the medial side or too loosely on the lateral side.

The remedy that was recommended some time ago, namely an outward rotation of the cutting guide such that in the posterior region less bone is removed laterally than medially, whereas anterior-laterally more bone is removed than on the anterior-medial side, also presents disadvantages, which the construction of the femoral slideway proposed in DE 197 16 879 A1 of the applicant is designed to eliminate. The crux of this solution is to rotate the anterior or ventral cut in the transverse plane.

However, this more recent solution also requires improvement with respect to optimizing the joint function in cooperation with the collateral ligaments in particular, especially in order to reduce the load imposed thereon.

SUMMARY OF THE INVENTION

It is thus the object of the invention to disclose a femoral slideway with further improved function, as well as a knee endoprosthesis system that can be efficiently constructed and employed and has such a femoral slideway as its essential element, and finally an advantageous arrangement comprising femoral slideway and femur-size template.

This object is achieved in its first, foremost aspect by a femoral slideway with the features described in the present application.

The invention includes the essential idea that it is advantageous to prepare for a knee-joint replacement by resecting more bone from the femur dorsally than is replaced by the implant (the femoral slideway). The "diminution" of the femoral slideway thus brought about in the dorsal region, in comparison to the original dimensions of the (resected) condyles or to a femoral slideway fitted in the conventional manner, produces an effective reduction of the turning radius of the tibial plate belonging to the prosthesis system and hence reduces the load on the collateral ligaments.

The decrease in the dimensions of the femoral slideway measured between the outermost, dorsoventrally opposed points on the condyle shell surfaces, in comparison to the previously customary dimensioning, is preferably in the range between 2 and 5%. This is achieved by constructing the associated femoral slideway/femur-size template arrangement in such a way that the distance separating one or more pegs on the femoral slideway from its dorsal sliding surface is smaller by 5-15%, in particular by about 10%, than the corresponding distance by which bores in the femur-size template for positioning the pegs are separated from the contact surface that is to be apposed to the dorsal condyle surfaces of the femur.

The distance between the dorsal sliding surfaces and the one or more pegs on the inside of the femoral slideway is preferably in the range between 24 and 34 mm and in particular is 29 mm, the chosen value advantageously being kept constant in a knee endoprosthesis system for covering a relevant joint-size range.

As noted above, the femoral slideway/femur-size template arrangement is constructed in such a way that the distance between one or more pegs on the femoral slideway and its dorsal sliding surface is smaller than the corresponding distance between bores in the femur-size template and the contact surface of the template by 5-15%, and in particular about 10%. Stated differently, the corresponding distance between bores in the femur-size template and the contact surface of the template is larger by 5-15%, an in particular about 10%, than the distance between one or more pegs on the femoral slideway and its dorsal sliding surface. Accordingly, the distance between the bores in the femur-size template and the contact surface of the template can be between 26.4 mm and 37.4 mm (i.e., 10% larger than the range of 24 mm to 34 mm between the dorsal sliding surface and the one or more pegs of the femoral slideway). In another embodiment, the distance between the bores in the femur-size template and the contact surface of the template can be about 32 mm (i.e., about 10% larger than a distance of 29 mm between the dorsal sliding surface and the one or more pegs of the femoral slideway). In yet another embodiment, the distance between the bores in the femur-size template and the contact surface of the template can be between 30.45 mm and 33.35 mm (i.e., 5%-15% larger than a distance of 29 mm between the dorsal sliding surface and the one or more pegs of the femoral slideway).

Another distinguishing feature of the proposed femoral slideway is that particular dimensions maintain a largely constant relationship to one another, regardless of the size of the actual prosthesis. For instance, the ratio a:c between the maximal dorsoventral extent and the maximal lateral extent of the femoral slideway is about 0.9±0.02. The patellar pit formed between the condyle shells preferably has a depth "b", measured from the dorsalmost point on the condyle shells, such that its ratio b:a to the maximal dorsoventral extent of the femoral slideway is in the range between 0.4 and 0.5, in particular is 0.44.

The patellar pit is thus lengthened in the dorsal direction, as a result of which the patella can be supported over a large area throughout its entire functional range of flexion.

This elongation of the patellar pit, which furthermore increases in accordance with the anatomy in implants of all sizes, allows for the fact that the patello-femoral contact surface in conventional femoral slideways has a relatively small bearing area. That is, in the region in which the patella leaves the trochlea and enters the intercondylar fossa, conventional femur components provide support only in the peripheral regions.

Furthermore, in the proposed femoral slideway the condyle shells are somewhat more strongly rounded in cross section (coronal section) than is the case in conventional femoral slideways. This modification was undertaken in the interest of improving the fit to the special tibia insert that belongs to a knee endoprosthesis system, but which is not within the scope of the invention.

The back surface of the femoral slideway, in one advantageous embodiment, bears a two-component Ti coating produced in a vacuum plasma procedure, consisting of a relatively thin, dense base layer and a several fold thicker, open-pored cover layer. The dense base layer allows the femoral slideway, which for example consists of CoCrMo, to become completely sealed to the bone and because it makes contact with the substrate over a large area, increases the stability of adhesion.

The open-pored and very rough surface of the cover layer provides ideal conditions for the growth of bony substance onto and into the carriage, producing a quasi "3-D interlocking" that can transmit pulling forces as well as pressure and transverse forces.

In accordance with one embodiment, a system for sizing and installing a femoral slideway implant is provided. The system comprises a femur size template comprising a base plate having at least one hole, at least one condyle engaging surface extending from the base plate, and a measurement tongue slidably mounted to the base plate, the tongue being movable between a plurality of discrete positions relative to the condyle engaging surface, wherein a first dimension is defined by a distance between the hole of the base plate and the condyle engaging surface. The system also comprises a femoral slideway implant comprising at least one condyle shell having an outer surface defining a dorsal sliding surface, a patellar shield located anterior to the condyle shell, and at least one peg on an inner surface of the implant and between the patellar shield and the condyle shell, wherein a second dimension is defined by a distance along a line extending perpendicularly between a plane tangent to the dorsal sliding surface and a longitudinal axis of the peg. The first dimension of the size template is larger than the second dimension of the implant by a predetermined amount.

In accordance with another embodiment, a system for installing a femoral slideway implant is provided. The system comprises a femur size template comprising at least one condyle engaging surface and a tongue configured to measure a maximal anterior posterior extent of the head of the femur. The system also comprises a femoral slideway implant comprising at least one condyle shell having an outer surface defining a dorsal sliding surface, and a patellar shield located anterior to the condyle shell, wherein a maximal anterior posterior extent of the condyle shell is less than the maximal anterior posterior extent of the femur.

BRIEF DESCRIPTION OF THE DRAWINGS

Additional advantages and useful features of the invention will be apparent from the subordinate claims and the following description of an exemplary embodiment with reference to the figures, wherein

DETAILED DESCRIPTION OF THE PREFERRED EMBODIMENTS

Figure 1:
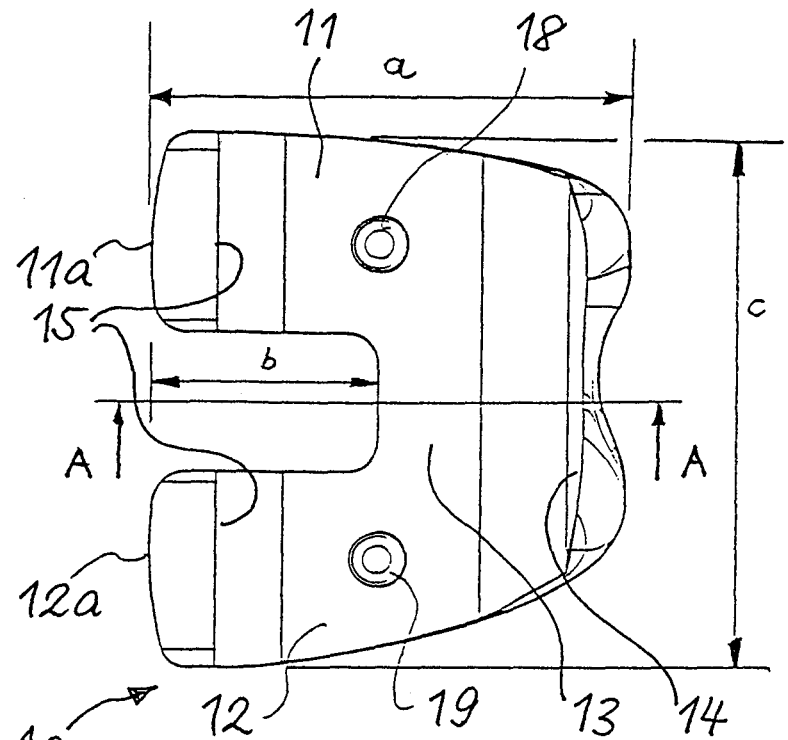
FIG. 1 is a view (from proximal) of a femoral slideway according to one embodiment of the invention.
Figure 2:
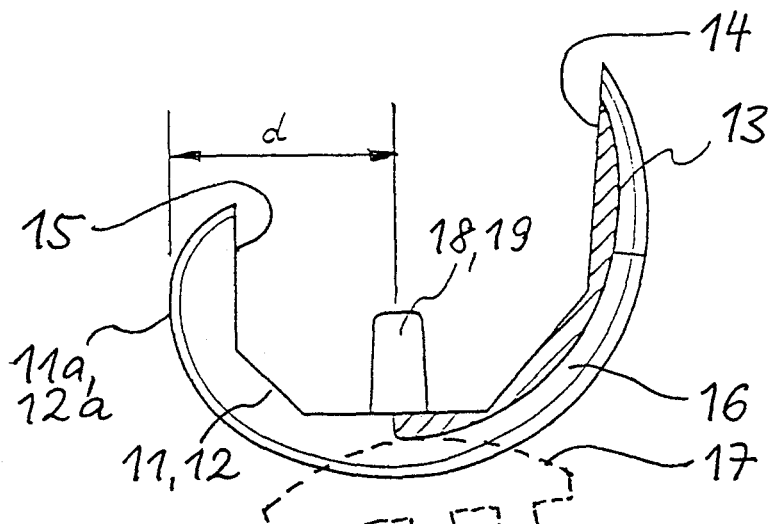
FIG. 2 shows the femoral slideway according to FIG. 1 in median section (sagittal section)

In FIGS. 1 and 2 the femur component 10, called a femoral slideway, of a knee endoprosthesis is shown. The femoral slideway 10 comprises two convexly curved condyle shells 11, 12 and a patellar shield 13, which connects the two condyle shells 11, 12 rigidly to one another.

The condyle shells 11, 12 and the patellar shield 13 in their interiors define anterior and posterior fitting surfaces 14, 15 that correspond to a femoral ventral and dorsal cut, respectively, and are associated with a ventral and a dorsal saw-cut surface produced at the distal end of the femur when the latter was resected for fitting of the femoral slideway. The convex outer shape of the condyle shells 11, 12 specifies dorsal sliding surfaces 11a, 12a in the posterior region, over which the corresponding surfaces of the tibia insert slide when the knee endoprosthesis is flexed. The patellar shield 13, which is recessed with respect to the convex outer surfaces of the condyle shells 11, 12, defines a so-called patellar pit 16, within which there is supported a patella component 17 of the knee endoprosthesis, which is indicated by a dashed outline in FIG. 2 and does not belong to the femoral slideway 10.

To assist anchoring and central placement of the femoral slideway 10 on the femur, on the inner surface of the femoral slideway two pegs 18, 19 are formed, the long axis of which is substantially parallel to the posterior fitting surface 15. These pegs project into holes in the femur, which have been drilled in the appropriate positions with the aid of a corresponding drilling template (see below), and this engagement gives the attachment of femoral slideway to bone greater stability than is provided by the fitting surfaces alone.

To ensure that the femoral slideway will function optimally as a replacement for destroyed sliding surfaces on the femur, the construction must reflect as accurately as possible the anatomical arrangements and dimensions, but also within the scope of the invention includes a specific modification that will now be explained.

One of the relevant dimensions of the femoral slideway is the maximal anterior-posterior or dorsoventral extent of the condyle shells 11, 12, a distance labeled "a" in FIG. 1. Another relevant dimension is the maximal lateral extent of the femoral slideway, i.e., the distance between the most lateral point on the lateral condyle shell 11 and the most medial point on the medial condyle shell 12, which in FIG. 1 is labeled "c". Also significant is the distance from the outermost posterior point on the dorsal sliding surfaces 11a, 12a of the condyle shells 11, 12 to the posterior bounding edge of the patellar shield 13, which in FIG. 1 is labeled "b". A final significant distance is that between the outermost posterior points on the dorsal sliding surfaces 11a, 12a and the long axis of the pegs 18, 19 (which lie in one and the same coronal plane), labeled "d" in FIG. 2. In the exemplary embodiment described here, the ratio a:c is 0.9 and the ratio b:a is 44. On grounds of biomechanics and surgical technique, it has proved useful to make the distance "d" (between sliding surface and peg axis) uniform for all sizes of femoral slideways used in a knee endoprosthesis system. In the present case, this distance is 29 mm.

Figure 3:
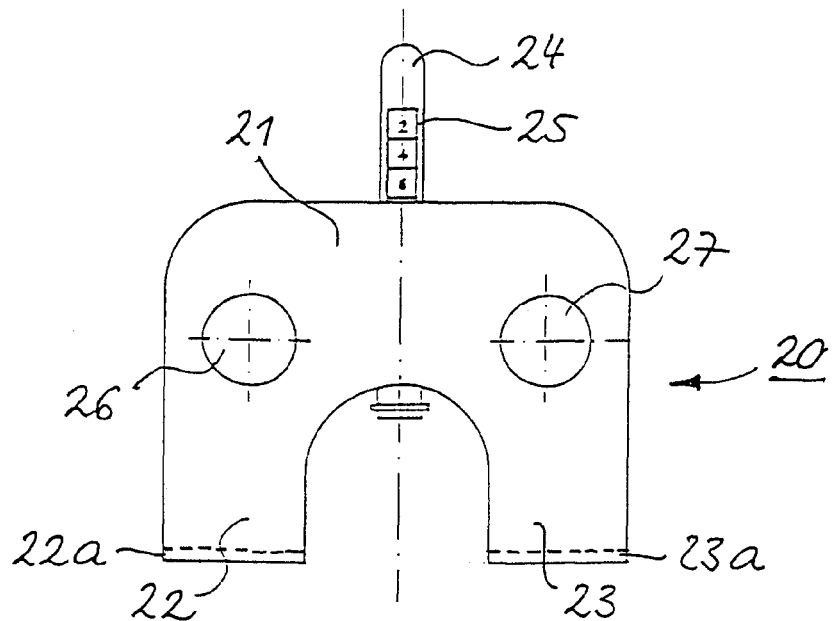
FIG. 3 is a plan view of an embodiment of a femur size template.
Figure 4:
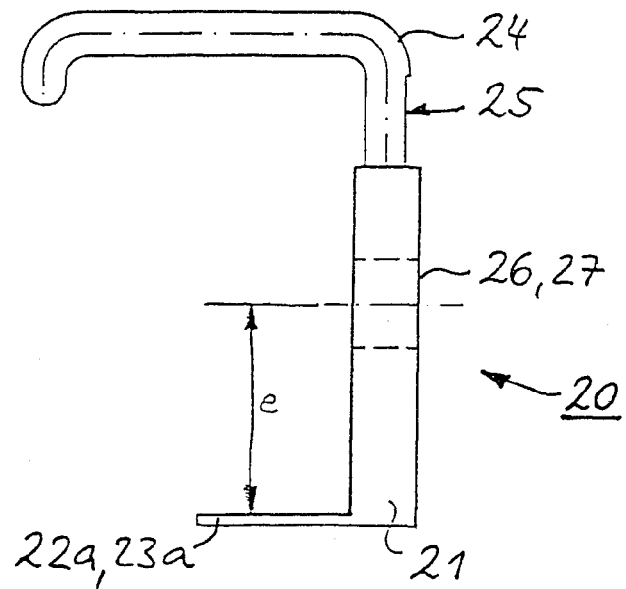
FIG. 4 is a side view of the latter.

To determine the correct femoral slideway size, a femur-size template 20 shown in FIGS. 3 and 4 is used. This comprises a basic part 21 with two flanks 22 and 23, each of which ends in a contact section 22a, 23a that is bent at a right angle and is apposed to the condyles of a femoral bone that is to be fitted with a femoral slideway (FIGS. 1 and 2).

In the middle of the basic part 21 a measurement tongue 24, bent at an angle in two places, is mounted so that it can be displaced in a direction perpendicular to the plane in which the contact sections 22a, 23a lie. The measurement tongue 24 is marked with a scale 25, which indicates the maximal anterior-posterior extent of the head of the femur, i.e. the condyles, and thus indicates to the doctor the required size of the implant. In the basic part 21 of the femur-size template 20 two peg-hole bores 26, 27 are provided, which—in accordance with a supplementary drilling-template function of the femur-size template—assist the positioning of peg-holes in the femur so that they correspond to the pegs 18, 19 of the femoral slideway 10, as shown in FIG. 1. The axes of the peg-hole bores 26, 27 are separated by a distance "e" from the contact surfaces of the contact sections 22a, 23a.

This distance—along with the distance "d" between the sliding surfaces and pegs on the femoral slideway 10 itself (cf FIG. 2)—is an additional relevant dimension in the concrete implementation of a knee endoprosthesis, for the following reason:

So that the above-mentioned peg-holes—which serve not only to position the implant but also to position the cutting guides used to produce the various saw cuts on the femur—can be drilled into the bone, drill bushes (not shown) are inserted into the peg-hole bores 26, 27.

It has proved advantageous, in particular from the viewpoint of reducing the load on the collateral ligaments during flexion of the artificial knee joint, to resect more bone dorsally on the femur than will be replaced there by the thickness of the dorsal parts of the condyle shells. For this reason the distance "e" is made larger than the corresponding distance "d" (FIG. 2). In the preferred embodiment, the relative distance reduction, i.e. the quantity (e−d)/d, is about 10%.

Figures 5A, 5B:
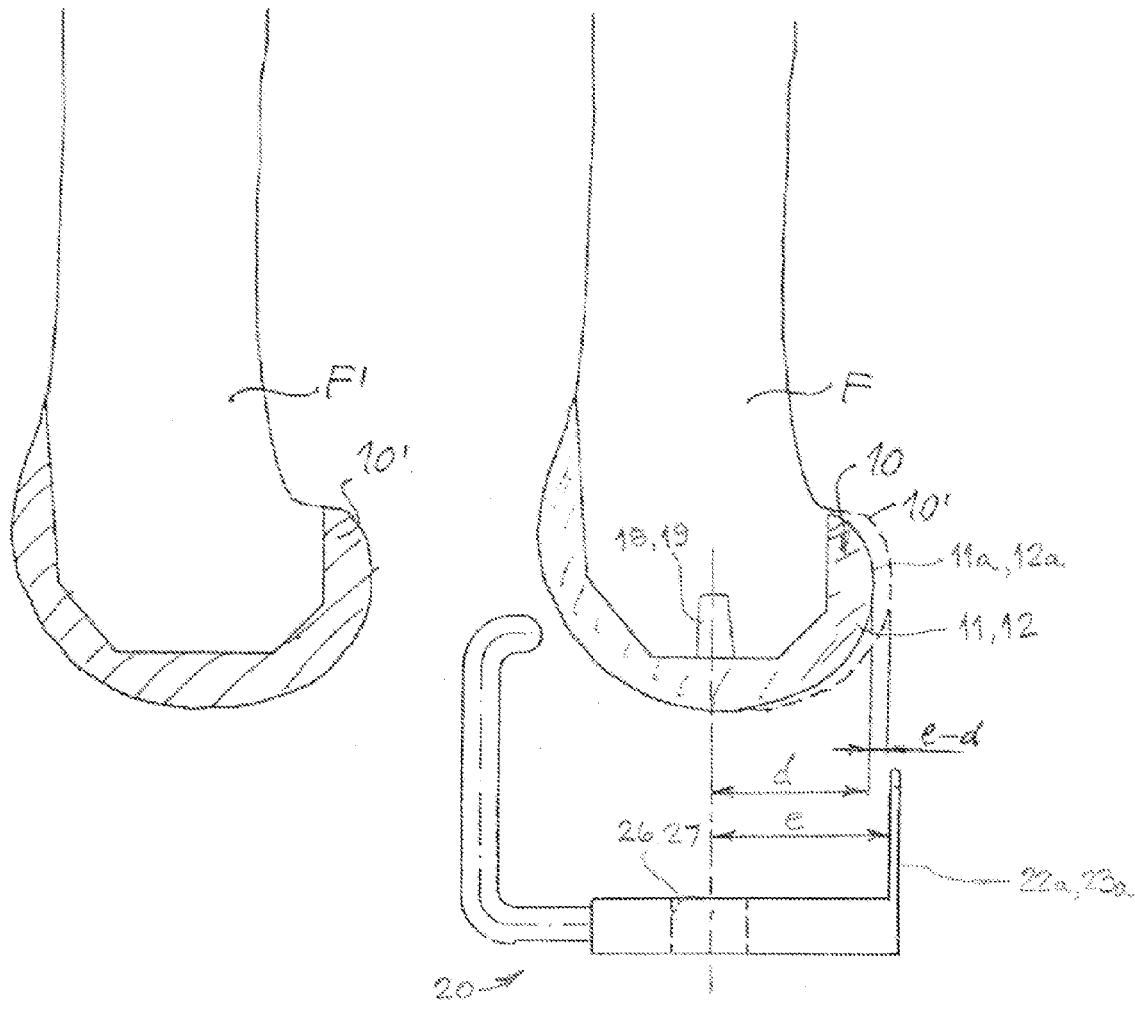
FIGS. 5a, 5b show a conventional arrangement of a femoral slideway on a femur in comparison to an arrangement proposed here.

The effect thus achieved can be seen in FIG. 5, where a sketch representing the conventional way of attaching a femoral slideway 10' to a femur F', shown in FIG. 5a, is compared with the representation in FIG. 5b of the arrangement proposed here. The anterior-posterior extent of the femoral slideway 10 in FIG. 5b, mounted on a femur F resected further in the dorsal region, is smaller by the amount (e−d) than in the conventional implant 10'.

Because the distance "e" is permanently specified by the femur-size template, which is used for all implants regardless of their size, and according to what has been stated above, the distance "d" in the embodiment of the femoral slideway is preferably kept constant for all implant sizes, the geometric relations will be slightly different for implants of different sizes. This is acceptable, however, in view of the advantages for manufacture and manipulation that such a system brings.

Figure 6A:
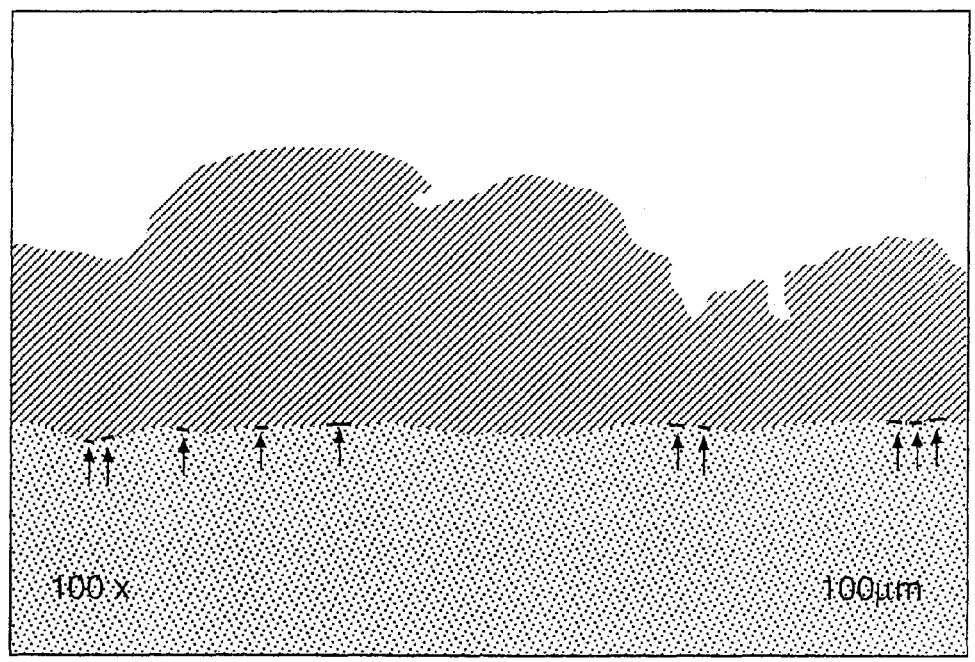
FIGS. 6a, 6b show scanning electron micrographs of a cross section of a conventional layered structure and of an embodiment of the layered structure proposed here for the back-surface coating of a femoral slideway.
Figure 6B:
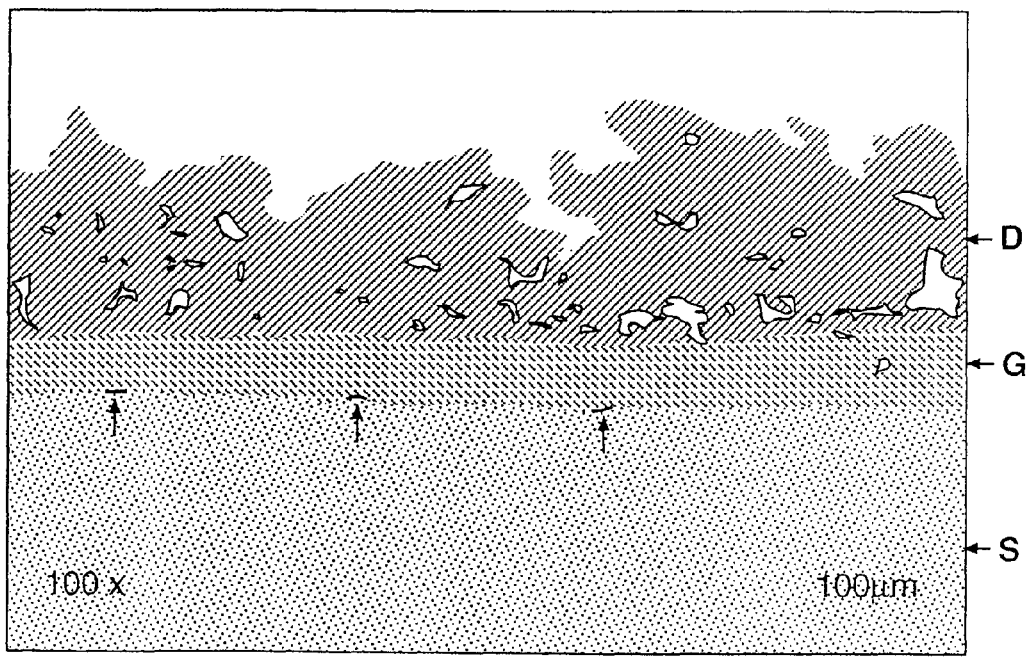

FIG. 6b shows—in comparison to a conventional femur carriage coating as shown in FIG. 6a—the appearance in the scanning electron microscope of a cross-section through a two-component titanium-coating construction consisting of a dense base layer G, about 50 μm thick, and an open-pored cover layer D averaging about 250 μm thick, on a CoCrMo substrate S. Although the thickness and average roughness of the coating according to FIG. 6b, which is applied by a vacuum plasma process, are comparable to those of the known, sprayed-on coating according to FIG. 6a, it should be emphasized that the former has a more open-pored structure and a considerably reduced number of interface defects (indicated in both pictures by vertical arrows).

Implementation of the invention is not limited to the exemplary embodiment described above, but can also incorporate modifications, which in particular include departures from the specified dimensions and ratio values.

LIST OF REFERENCE NUMERALS 10, 10' Femoral slideway
11, 12 Condyle shells
11a, 12a Dorsal sliding surfaces
13 Patellar shield
14 Anterior fitting surface
15 Posterior fitting surface
16 Patellar pit
17 Patella component
18, 19 Peg
20 Femur-size template
21 Basic part
22, 23 Flanks
22a, 23a Contact sections
24 Measurement tongue
25 Scale markings
26, 27 Peg-hole bores
a, b, c, d, e Distances
A-A Plane of section
D Cover layer
F, F' Femur (shaped)
G Base layer
S Substrate

What is claimed is:

1. A system for sizing and installing a femoral slideway implant, comprising:
   a femur size template comprising:
   a base plate having at least one hole,
   at least one condyle engaging surface extending from the base plate, and a measurement tongue slidably mounted to the base plate, the tongue being movable between a plurality of discrete positions relative to the condyle engaging surface,
   a first dimension of the femur size template is defined by a distance between a central axis of the hole in the base plate and the condyle engaging surface; and
   a femoral slideway implant comprising:
   at least one condyle shell having an outer dorsal sliding surface defining an outermost posterior point of the at least one condyle shell,
   a patellar shield located anterior to the at least one condyle shell,
   at least one peg on an inner surface of the implant and located between the patellar shield and the condyle shell, and
   a second dimension of the femoral slideway implant is defined by a distance between a plane tangent to the dorsal sliding surface at the outermost posterior point of the at least one condyle shell and a longitudinal axis of the at least one peg, and
   the first dimension of the femur size template is larger than the second dimension of the femoral slideway implant by a permanently specified distance that defines a fixed absolute difference between the first dimension and the second dimension; and wherein the first dimension is a permanently specified distance of the femur size template irrespective of the size of the femoral slideway implant; and wherein the femoral slideway implant comprises a plurality of femoral slideway implants of different sizes, wherein the second dimension is a constant amount for the plurality of femoral slideway implants.

2. The system of claim 1, wherein the at least one condyle shell comprises first and second convexly curved condyle shells.

3. The system of claim 2, wherein a patellar pit between the condyle shells of the femoral slideway has a depth measured from a most dorsal point on the condyle shells that has a ratio in the range of about 0.4 to 0.5 in comparison to a maximal anterior-posterior extent of the femoral slideway.

4. The system of claim 1, wherein the first dimension is at least 5% larger than the second dimension.

5. The system of claim 1, wherein the first dimension is between 5% and 15% larger than the second dimension.

6. The system of claim 5, wherein the first dimension is about 10% larger than the second dimension.

7. The system of claim 1, further comprising a third dimension defined by a distance between the plane tangent to the dorsal sliding surface and a ventral surface of the patellar shield, the third dimension corresponding to one of the discrete positions of the measurement tongue.

8. The system of claim 1, wherein the base plate and the at least one condyle engaging surface are defined by a single-piece unitary structure.

9. The system of claim 1, wherein the first dimension is defined by a perpendicular distance between the central axis of the hole and the condyle engaging surface.

10. The system of claim 1, wherein the at least one condyle engaging surface has a permanently fixed position on the base plate with respect to the at least one hole.

11. A system for installing a femoral slideway implant, comprising:
a femur size template comprising:
at least one condyle engaging surface, a measurement tongue configured to measure a maximal anterior posterior extent of at least one condyle of the femur, said at least one condyle abutting the condyle engaging surface, said measurement tongue being movable between a plurality of discrete positions relative to the at least one condyle engaging surface; and
a base plate between said condyle engaging surface and said tongue, the base plate having at least one hole configured to receive a drill,
a first dimension of the femur size template is defined by a distance between a central axis of the hole in the base plate and the condyle engaging surface; and
a femoral slideway implant comprising:
at least one condyle shell having an outer dorsal sliding surface defining an outermost posterior point of the at least one condyle shell,
a patellar shield located anterior to the at least one condyle shell,
at least one peg on an inner surface of the implant and located between the patellar shield and the at least one condyle shell, the peg configured to mount in a hole in a condyle measured by the template and drilled into the condyle through the at least one hole in the base plate,
a second dimension of the femoral slideway implant is defined by a distance between a plane tangent to the dorsal sliding surface at the outermost posterior point of the at least one condyle shell and a longitudinal axis of the at least one peg, and a maximal anterior posterior extent of the condyle shell is less than the maximal anterior posterior extent of the at least one condyle of the femur by a fixed amount, and the first dimension of the femur size template is larger than the second dimension of the femoral slideway implant to thereby define a fixed absolute difference between the first dimension and the second dimension; and wherein the first dimension is a permanently specified distance of the femur size template irrespective of the size of the femoral slideway implant; and wherein the femoral slideway implant comprises a plurality of femoral slideway implants of different sizes, wherein the second dimension is a constant distance for the plurality of femoral slideway implants.

12. The system of claim 11, wherein the at least one condyle shell comprises first and second convexly curved condyle shells.

13. The system of claim 11, wherein a patellar pit between the condyle shells of the femoral slideway has a depth measured from the from a most dorsal point on the condyle shells that has a ratio in the range of about 0.4 to 0.5 in comparison to a maximal anterior-posterior extent of the femoral slideway.

14. The system of claim 11, wherein the maximal anterior posterior extent of the at least one condyle of the femur is between 5% and 15% larger than the maximal anterior posterior extent of the condyle shells.

15. The system of claim 14, wherein the maximal anterior posterior extent of the at least one condyle of the femur is 10% larger than the maximal anterior posterior extent of the condyle shells.

16. The system of claim 11, wherein the tongue slidably engages the at least one condyle, the tongue being movable between a plurality of discrete positions relative to the condyle engaging surface, wherein a first dimension is defined by a distance between a plane tangent to a dorsal sliding surface of the at least one condyle and a ventral surface of a patellar shield of the femur; the first dimension corresponding to one of the discrete positions of the tongue such that each discrete position of the tongue indicates a required size for the femoral slideway.

17. The system of claim 11, wherein the base plate and the at least one condyle engaging surface are defined by a single-piece unitary structure.

18. The system of claim 11, wherein the first dimension is at least 5% larger than the second dimension.

19. The system of claim 11, wherein the first dimension is between 5% and 15% larger than the second dimension.

20. The system of claim 11, wherein the first dimension is about 10% larger than the second dimension.

21. The system of claim 11, wherein the at least one condyle engaging surface is permanently attached to the base plate to provide the permanently specified distance of the first dimension of the femur template.

22. A system, comprising:
a plurality of femoral slideway implants, each comprising:
at least one condyle shell having an outer dorsal sliding surface defining an outermost posterior point of the at least one condyle shell,
a patellar shield located anterior to the at least one condyle shell;
at least one peg on an inner surface of the implant and located between the patellar shield and the at least one condyle shell; and
a first dimension defined by a distance between a plane tangent to the dorsal sliding surface at the outermost posterior point of the at least one condyle shell and a longitudinal axis of the at least one peg;

wherein each of the plurality of femoral slideway implants has a different implant size; and wherein the first dimension is constant throughout the plurality of femoral slideway implants irrespective of the implant size;

a femur size template for determining an appropriate implant size corresponding to one of the different implant sizes and for installing the femoral slideway implant having the implant size corresponding to the appropriate implant size, the femur size template comprising:

a base plate having at least one hole;

at least one condyle engaging surface extending from the base plate, the at least one condyle surface having a permanently fixed location with respect to the at least one hole in the base plate;

a measurement tongue slidably mounted to the base plate, the tongue being movable between a plurality of discrete positions relative to the condyle engaging surface; and a second dimension defined by a distance between a central axis of the hole in the base plate and the permanently fixed location of the at least one condyle engaging surface;

wherein the second dimension of the femur size template is larger than the constant first dimension of the plurality of the femoral slideway implants by a permanently specified distance.

23. The system of claim 22, wherein each of the femoral slideway implants has a maximal anterior-posterior extent, wherein each of the implant sizes has a different maximal anterior-posterior-extent, and wherein each of the plurality of discrete positions of the measurement tongue corresponds to the maximal anterior-posterior extent of one of the implant sizes.

* * * * *